United States Patent [19]

Marin et al.

[11] Patent Number: 5,447,714

[45] Date of Patent: Sep. 5, 1995

[54] METHOD FOR REPELLING AEDES AEGYPTAE USING CARBOCYCLIC KETONES, ALDEHYDES AND ESTERS

[75] Inventors: Anna B. Marin, Leonardo; Craig B. Warren, Rumson, both of N.J.; Jerry F. Butler, Gainesville, Fla.

[73] Assignees: International Flavors & Fragrances Inc., New York, N.Y.; The University of Florida, Gainesville, Fla.

[21] Appl. No.: 394,250

[22] Filed: Feb. 24, 1995

Related U.S. Application Data

[62] Division of Ser. No. 228,350, Apr. 15, 1994, which is a division of Ser. No. 157,420, Nov. 26, 1993, Pat. No. 5,354,783.

[51] Int. Cl.⁶ .............. A01N 25/20; A01N 35/02; A01N 35/04; C11D 9/50
[52] U.S. Cl. ............... 424/40; 424/DIG. 10; 424/405; 424/409; 514/688; 514/693; 514/919; 43/124; 43/132.1
[58] Field of Search ......... 424/40, 405, 409, DIG. 10; 514/688, 693, 919; 43/124, 125, 132.1; 422/5

[56] References Cited

U.S. PATENT DOCUMENTS

| | | | |
|---|---|---|---|
| 4,507,225 | 3/1985 | Sprecker et al. | 252/8.6 |
| 4,582,634 | 4/1986 | Sprecker et al. | 252/8.6 |

OTHER PUBLICATIONS

Kin, "Chemicals Evaluated as Insecticides and Repellents at Orlando, Florida", U.S. Department of Agriculture, Agricultural Research Service, Agriculture Handbook No. 69, pp. 52, 53, 54 and Title page attached (of specific interest is Item No. 1117, the methyl ester of anthranilic acid), 1954.

Beroza, "Materials Evaluated as Insecticides, Repellents and Chemostrerilants at Orlando and Gainesville, Florida, 1952-1964", Agriculture Handbook No. 340, Agricultural Research Service, United States Department of Agriculture, issued Aug. 1967, p. 46 and Title page attached (of specific interest are Item Nos. 815-820, various esters of anthranilic acid).

*Primary Examiner*—Allen J. Robinson
*Assistant Examiner*—John D. Pak
*Attorney, Agent, or Firm*—Arthur L. Liberman

[57] ABSTRACT

Described is an insect repellent candle containing a candle base and intimately admixed therewith an insect repelling quantity of at least one composition selected from the group consisting of:

(i) mixture of aldehydes defined according to the structure:

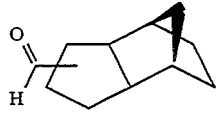

containing from 60-40 mole percent of the compound having the structure:

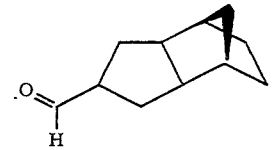

and from 40-60 mole percent of the compound having the structure:

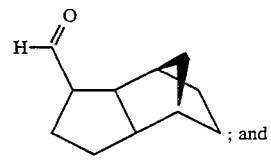

; and and
(ii) ketone having the structure:

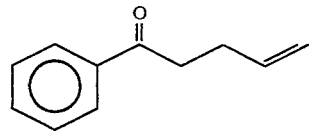

1 Claim, 6 Drawing Sheets

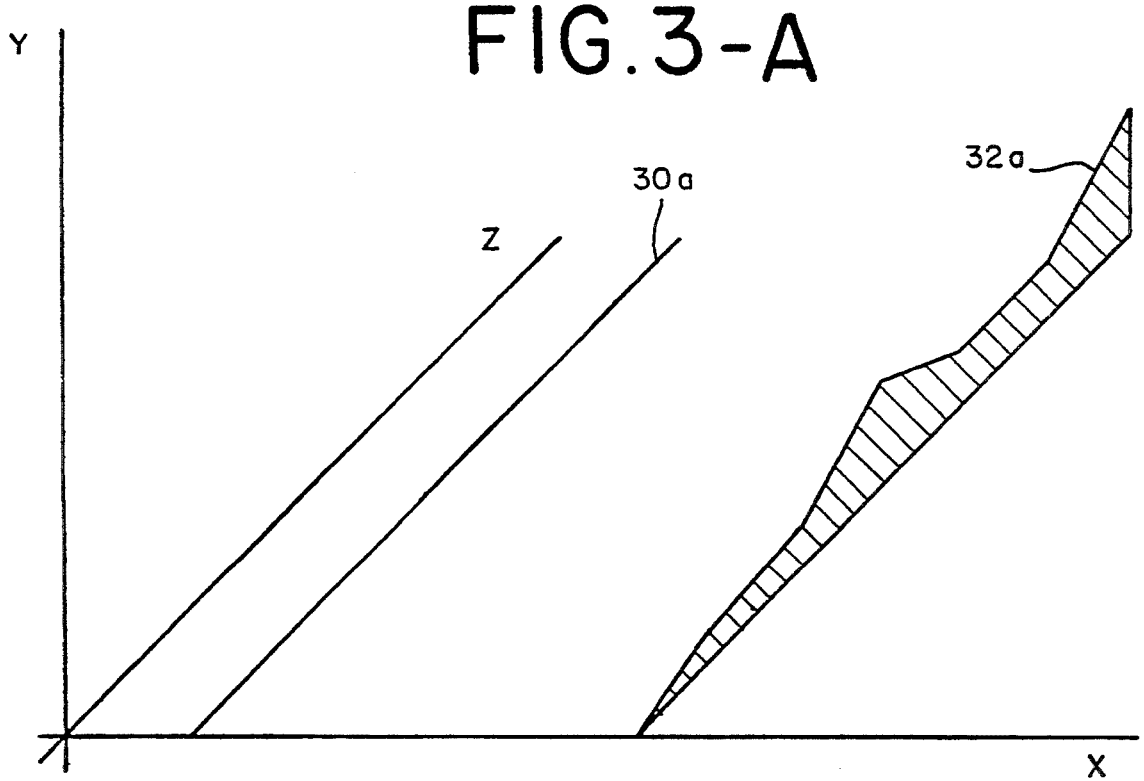
FIG.3-A
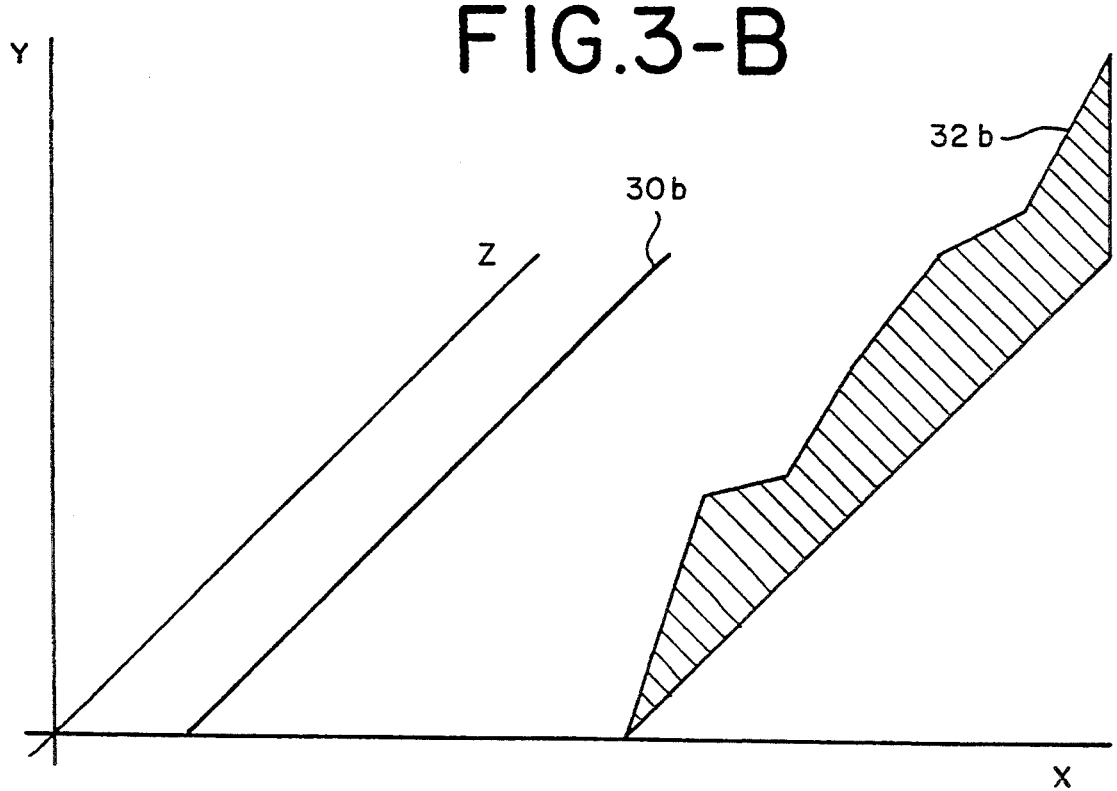
FIG.3-B

FIG.3-C
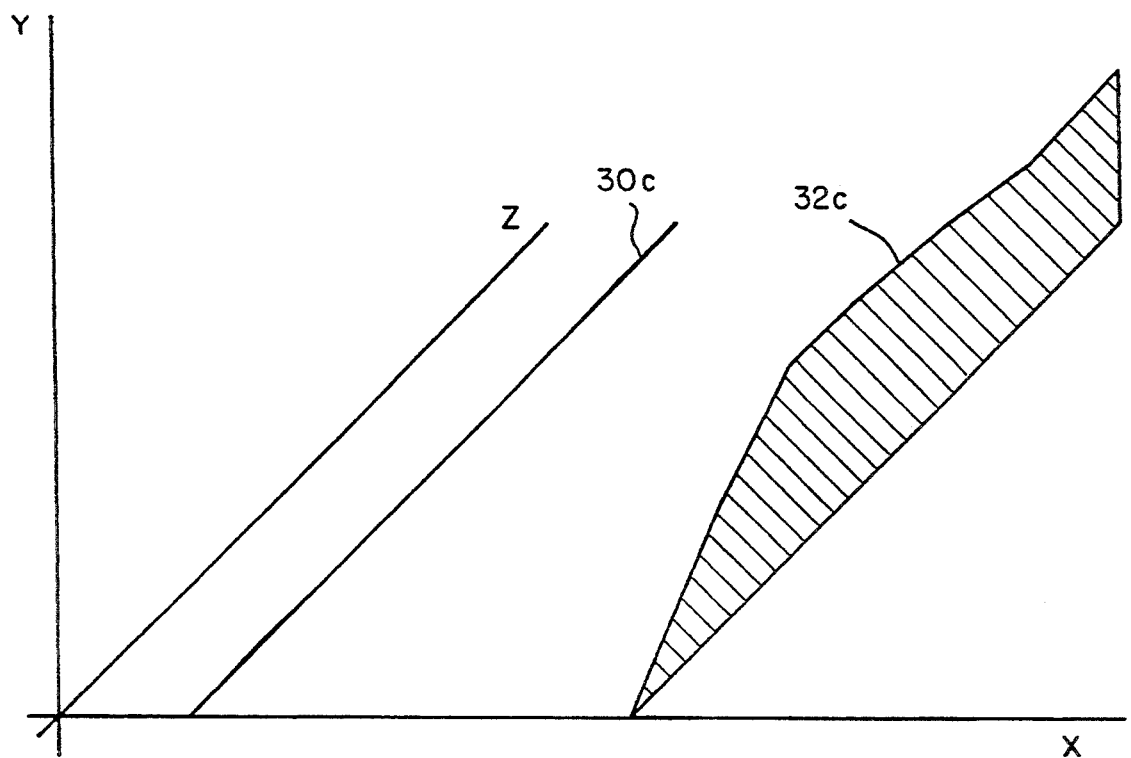

FIG.4-A
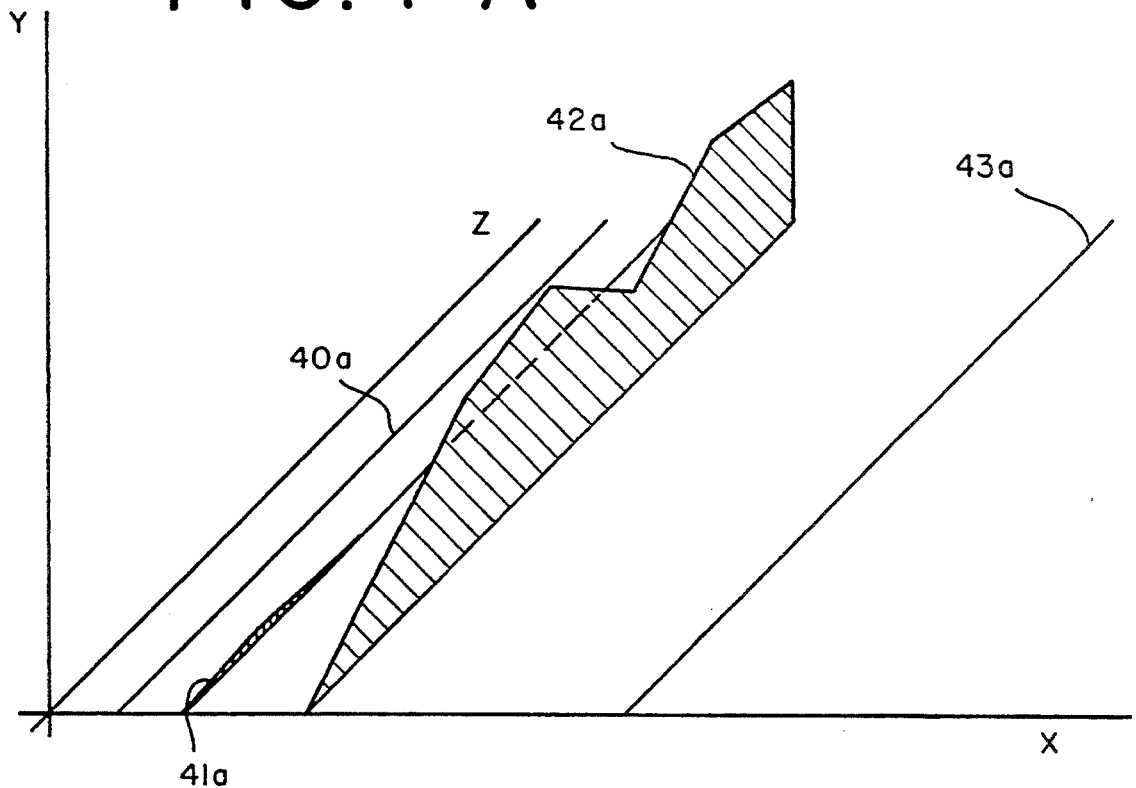
FIG.4-B
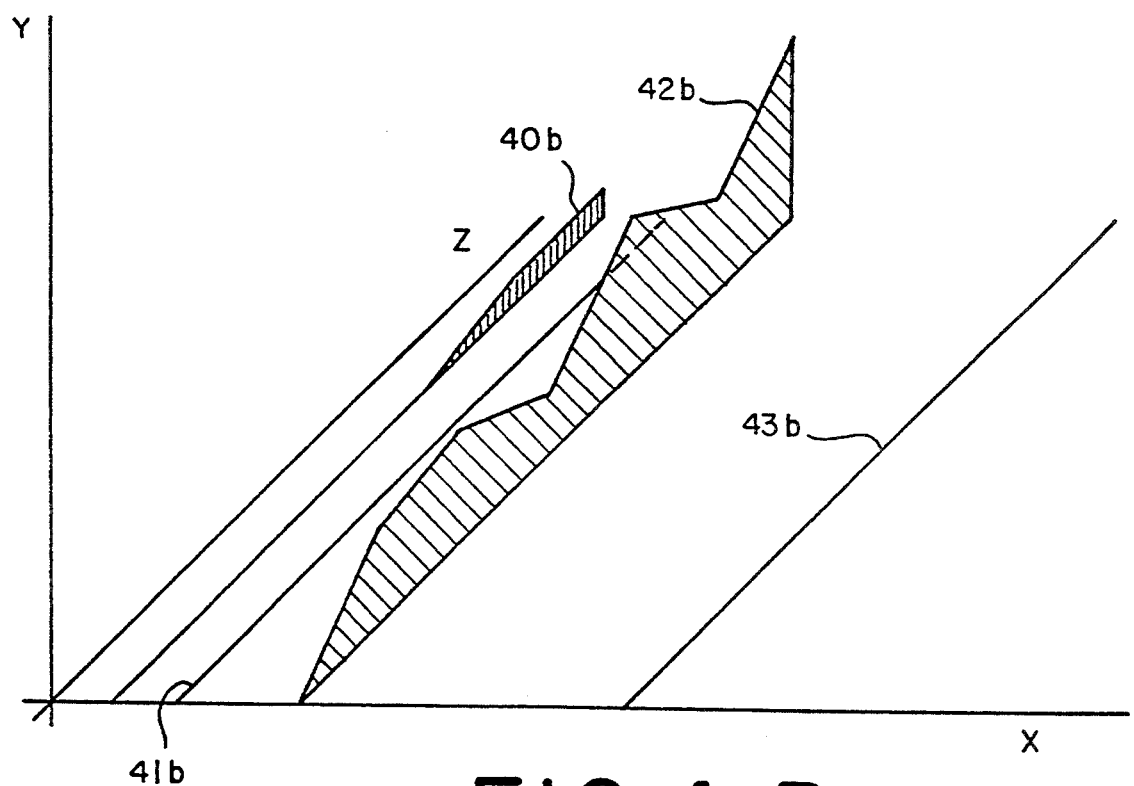

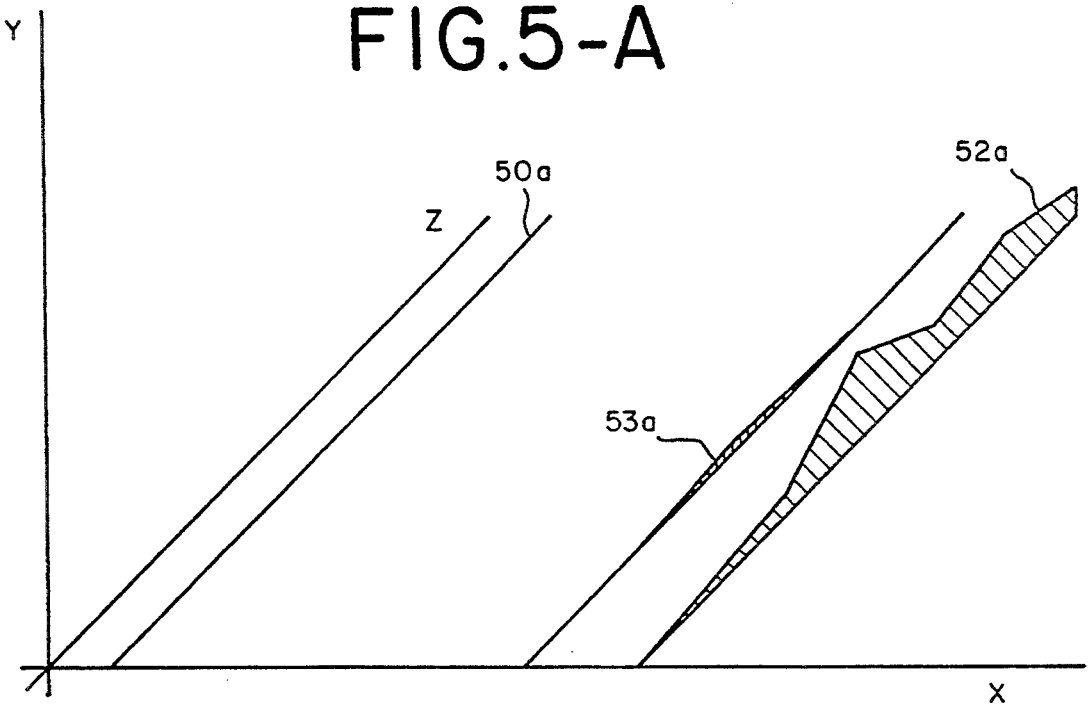
FIG.5-A
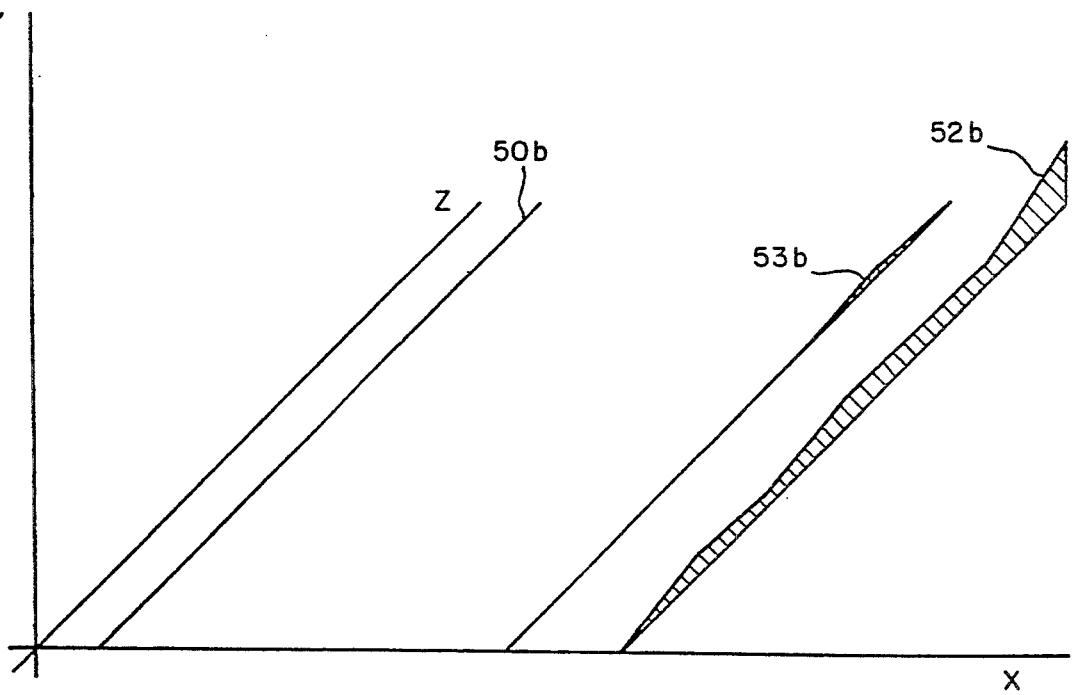
FIG.5-B

METHOD FOR REPELLING AEDES AEGYPTAE USING CARBOCYCLIC KETONES, ALDEHYDES AND ESTERS

This is a divisional of application Ser. No. 08/228,350, filed Apr. 15, 1994, which is a divisional of application for U.S. Letters Patent Ser. No. 08/157,420 filed on Nov. 26, 1993, now U.S. Pat. No. 5,354,783 issued on Oct. 11, 1994.

BACKGROUND OF THE INVENTION

This invention relates to the use of certain carbocyclic, ketones, aldehydes and esters in repelling mosquitoes (*Aedes aegyptae*) which carbocyclic compounds have the structures:

(i) methyl anthranilate:

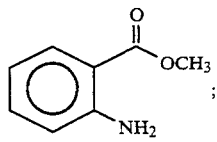

(ii) MELOZONE TM:

(iii) LAVONAX TM:

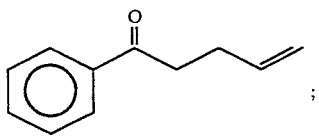

and (iv) CYCLEMONE A TM the mixture of compounds having the structures:

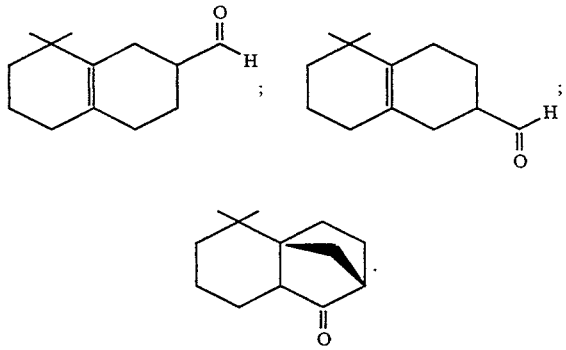

The need for safe, non-toxic and aesthetically pleasing materials capable of efficaceously repelling blood feeding arthropods such as the mosquito species *Aedes aegyptae* is obvious particularly in view of the fact that such blood feeding arthropods as *Aedes aegyptae* carry a number of harmful viruses; harmful to various mammalian species.

Carbocyclic ketones and esters have been demonstrated to be useful in repelling *Aedes aegyptae* as set forth in Wilson, et al, I, U.S. Pat. No. 5,165,926 wherein compounds defined according to the structures:

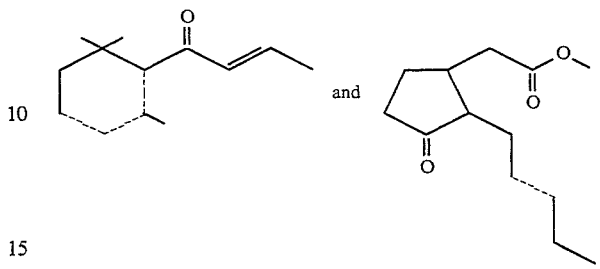

have been shown to be useful in repelling *Aedes aegyptae* (wherein in each of the compounds one of the dashed lines is a carbon-carbon double bond and each of the other of the dashed lines are carbon carbon single bonds).

On the other hand, Wilson, et al, II, U.S. Pat. No. 4,801,446 have shown that the compound having the structure:

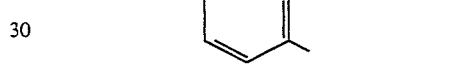

is an attractant for insects such as (*Musca domestica L.* (Diptera:Muscidae) (the house fly).

The carbocyclic aldehydes, ketones and esters of our invention have properties and structures different in kind from those of the prior art. The efficacy of the carbocyclic ketones, aldehydes and esters of our invention is unexpected, unobvious and advantageous for the purposes of repelling *Aedes aegyptae* from three dimensional spaces inhabited by such *Aedes aegyptae*.

SUMMARY OF THE INVENTION

Our invention sets forth processes for repelling the mosquito species *Aedes aegyptae* consisting essentially of exposing a three dimensional space inhabited by said *Aedes aegyptae* to an *Aedes aegyptae*-repelling effective concentration and quantity of at least one of the following carbocyclic aldehydes, ketones or esters:

(i) methyl anthranilate having the structure:

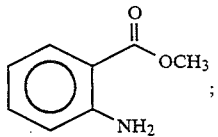

(ii) MELOZONE TM defined according to the structure:

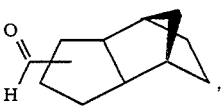

which is a mixture of compounds having from 60–40 mole percent of the compound having the structure:

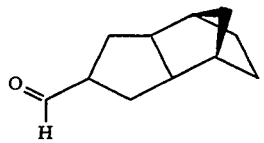

and from 40–60 mole percent of the compound having the structure:

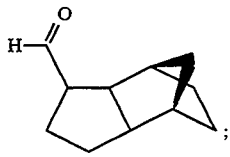

(iii) LAVONAX ™ having the structure:

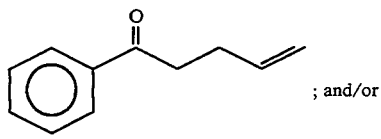

; and/or and/or
(iv) CYCLEMONE A ™ a mixture of compounds having the structures:

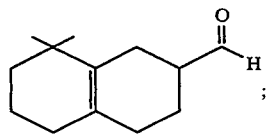

containing from 45–60 mole percent of the compound having the structure:

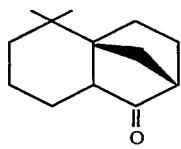

from 15–20 mole percent of the compound having the structure:

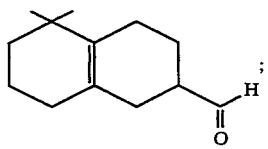

and from 25–35 mole percent of the compound having the structure:

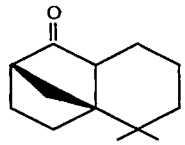

The methyl anthranilate MELOZONE ™, LAVONAX ™ and CYCLEMONE A ™ can be used separately or can be used in various combinations for the purpose of repelling *Aedes aegyptae*.

The carbocyclic ketone, aldehydes and esters of our invention can be used in the form of sprays (as in aerosol cans); lotions for coating on skin; it can be admixed with wax and formulated into candle articles; or they can be incorporated into soap and caused the user of the soap in a washing procedure to impart insect repellency to said user of the soap subsequent to the washing procedure.

BRIEF DESCRIPTION OF THE DRAWINGS

FIG. 3A is a series of graphs depicted in three dimensions (in a rectangular mode for the "x" and "y" axes) showing the relative attractiveness or repellency of methyl anthranilate having the structure:

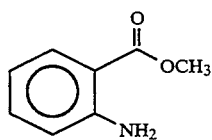

Figure 1:
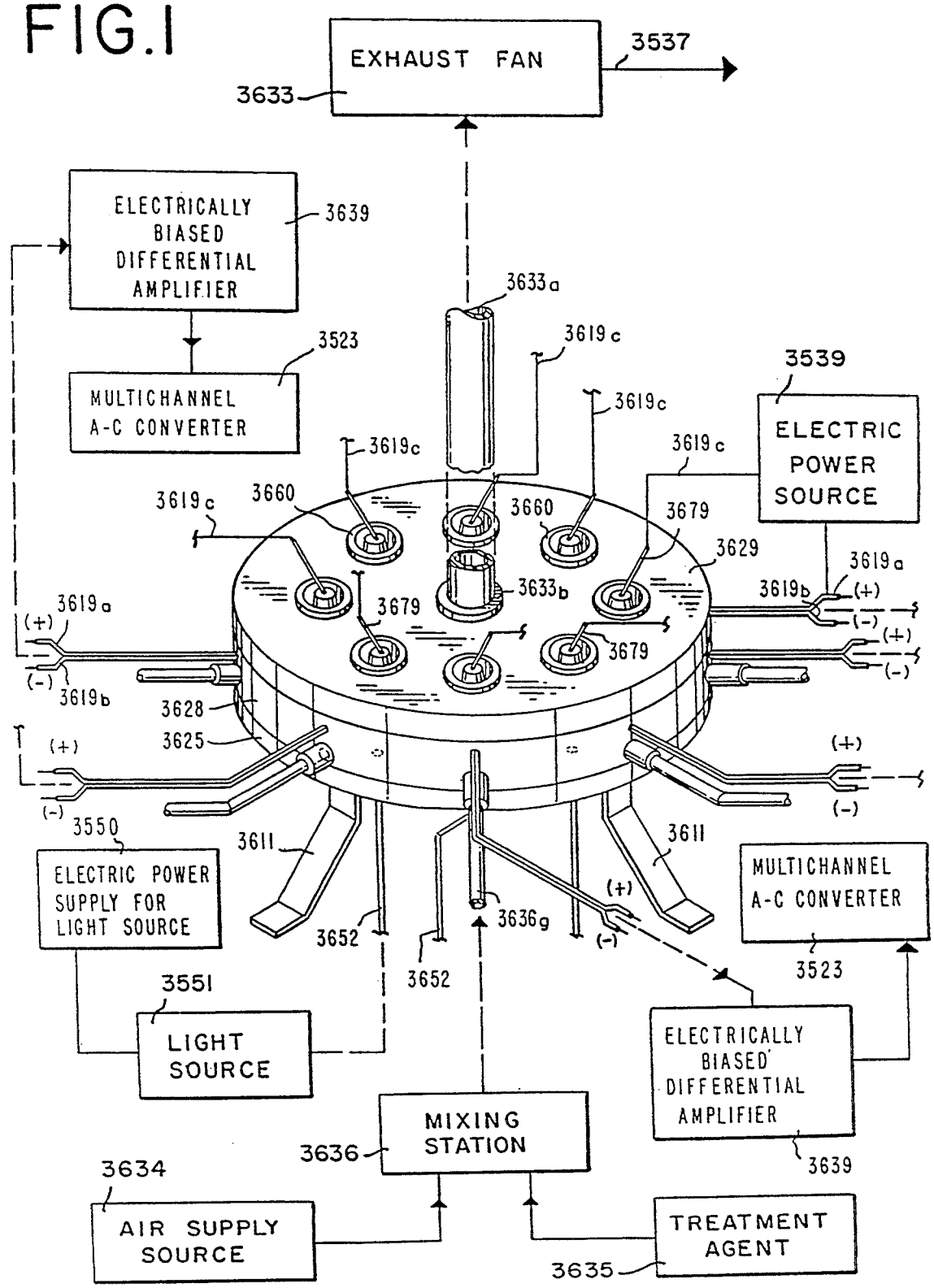
FIG. 1 is a schematic diagram of an embodiment of an olfactometer apparatus (disclosed in detail in U.S. Pat. No. 5,165,926 issued on Nov. 24, 1992 incorporated herein by reference) useful in ascertaining attractancy or repellency of the carbocyclic ketones, aldehydes and esters as repellents against mosquitoes (*Aedes aegyptae*) indicating in schematic block flow diagram form the utilization of computer-assisted efficacy measuring apparatus; and also showing in block flow diagram form the inter-relationship of the air and treatment agent mixing station with the entry ports for the resulting air-treatment mixture into the olfactometer apparatus.

and air for mosquitoes (*Aedes aegyptae*). The graphs are based on experiments run for a period of one hour with 6 intervals of 10 minutes each using as the insect to be tested the mosquito (*Aedes aegyptae*). The results are tabulated in Table I(A), infra.

FIG. 3B is a series of graphs depicted in three dimensions (in a rectangular mode for the "x" and "y" axes) showing the relative attractiveness or repellency for mosquitoes (*Aedes aegyptae*) of methyl anthranilate having the structure:

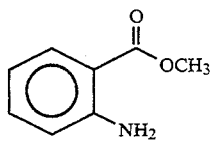

and air. The graphs are based on experiments run for a total of 6 hours with 6 intervals of 1 hour each. The results are tabulated in Table I(B), infra.

FIG. 3C is a series of graphs depicted in three dimensions (in a rectangular mode for the "x" and "y" axes) showing the relative attractiveness or repellency for mosquitoes (*Aedes aegyptae*) of methyl anthranilate and air. The graphs are based on experiments run for a total of 12 hours with 6 intervals of 2 hours each. The results are tabulated in Table I(C), infra.

FIG. 4A is a series of graphs depicted in three dimensions (in a rectangular mode for the "x" and "y" axes) showing the relative attractiveness or repellency for mosquitoes (*Aedes aegyptae*) of LAVONAX TM having the structure:

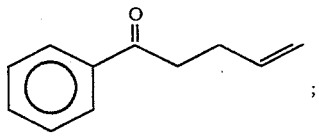

and MELOZONE TM defined according to the structure:

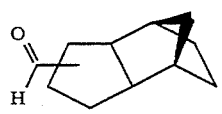

(a 50:50 mixture of the compounds having the structures:

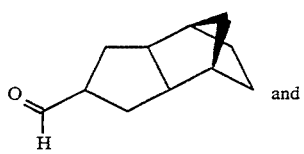
and
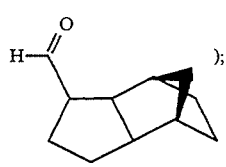
);

and a mixture containing 81 mole percent of geraniol having the structure:

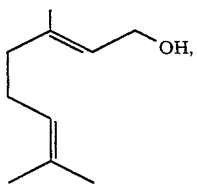

14 mole percent of citronellol having the structure:

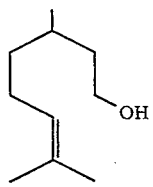

and 5% nerol having the structure:

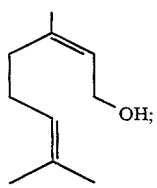

and air. The graphs are based on experiments run for a total of 1 hour with 6 intervals of 10 minutes each. The results are tabulated in Table II(A), infra.

FIG. 4B is a series of graphs depicted in three dimensions (in a rectangular mode for the "x" and "y" axes) showing the relative attractiveness or repellency for mosquitoes (*Aedes aegyptae*) of LAVONAX TM; MELOZONE TM; air; and the mixture of compounds, to wit:

81 mole percent geraniol having the structure:

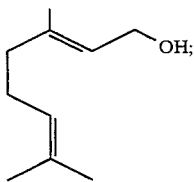

4 mole percent citronellol having the structure:

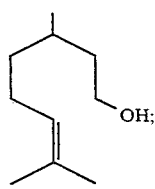

and 5 mole percent nerol having the structure:

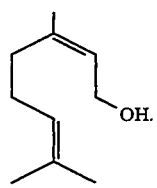

The graphs are based on experiments run for a total of 6 hours with 6 intervals of 1 hour each. The results are tabulated in Table II(B), infra.

FIG. 5A is a series of graphs depicted in three dimensions in a rectangular mode for the "x" and "y" axes) showing the relative attractiveness or repellency of:

"CYCLEMONE A TM a mixture containing 51 mole percent of the compound having the structure:

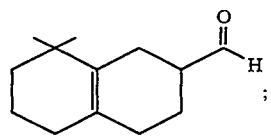

17 mole percent of the compound having the structure:

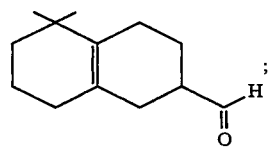

and 32 mole percent of the compound having the structure:

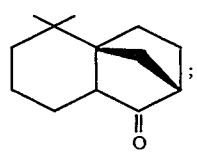

air and a mixture containing 81.8% geraniol having the structure:

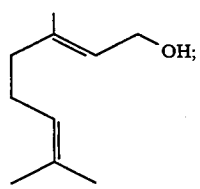

11.66 mole percent citronellol having the structure:

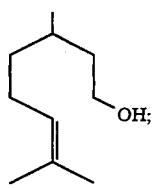

and 6.53 mole percent nerol having the structure:

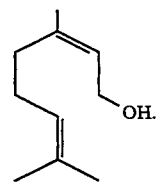

The graphs are based on experiments run for a total of 1 hour with 6 intervals of 10 minutes each. The results are tabulated in Table III(A), infra.

FIG. 5B is a series of graphs depicted in three dimensions (in a rectangular mode for the "x" and "y" axes) showing the relative attractiveness or repellency of CYCLEMONE A TM; air; and a mixture containing 81.8% geraniol having the structure:

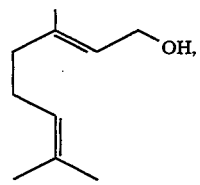

11.66 mole percent citronellol having the structure:

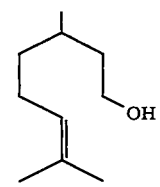

and 6.53 mole percent nerol having the structure:

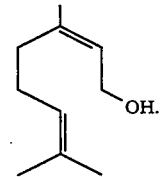

The graphs are based on experiments run for a total of 6 hours with 6 intervals of 1 hour each. The results are tabulated in Table III(B), infra.

THE INVENTION

Our invention relates to a method of repelling mosquitoes (*Aedes aegyptae*) consisting of the step of exposing a three dimensional space inhabited by such (*Aedes aegyptae*) in an *Aedes aegyptae* repelling effective concentration and quantity of at least one of the following materials:

(i) methyl anthranilate having the structure:

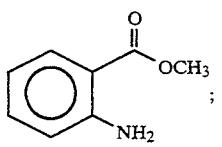

(ii) MELOZONE ™ a mixture of compounds defined according to the structure:

containing from 60–40 mole percent of the compound having the structure:

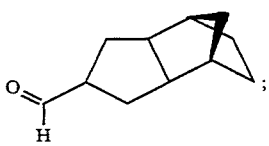

and from 40–60 mole percent of the compound having the structure:

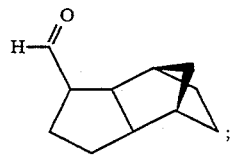

(iii) LAVONAX ™ having the structure:

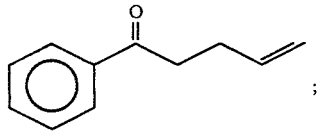

and (iv) CYCLEMONE A ™, a mixture of compounds containing from 45–60 mole percent of the compound having the structure:

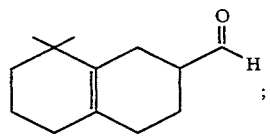

from 15–20 mole percent of the compound having the structure:

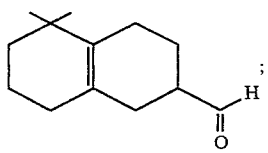

and from 25–35 mole percent of the compound having the structure:

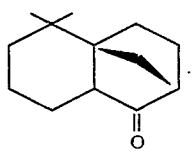

Our invention is also related to the use of the foregoing insect repellent compositions in personal soap compositions, for example, the insect repellent soap composition described in U.S. Pat. No. 4,707,496 issued on Nov. 17, 1987, the specification for which is incorporated by reference herein. Thus, in applying the teachings of U.S. Pat. No. 4,707,496 to our invention, a topical insect repellent soap composition and a method of protection using such a composition is described where the insect repellent soap composition comprises:

(i) from 63.0 up to 99.5% by weight of a soap mixture containing from 4.1 to 7% by weight of a soap of caprylic acid, from 3.8 to 7% of a soap of capric acid, from 32.1 to 45% of a soap of laurie acid, from 12 to 17.5% by weight of a soap of myristic acid, from 5.0 up to 10% by weight of a soap of palmitic acid, from 1.6 to 3% by weight of a soap of stearic acid, from 3.5 to 5% by weight of a soap of oleic acid and from 0.9 to 5% by weight of a soap of linoleic acid;

(ii) from 0.1 up to 2% by weight of $C_8$–$C_{18}$ straight chain fatty acids;

(iii) from 10 up to 30% by weight of at least one of the repellent chemicals of our invention, e.g., at least one of the carbocyclic ketones, aldehydes and esters set forth, supra; and (iv) from 0.2 up to 5% by weight of an effective residual insecticide as described in U.S. Pat. No. 4,707,496.

Other insect repellent soaps can be produced by adding one or more of the carbocyclic ketones, aldehydes and esters of our invention to one or more of the compositions described and claimed in U.S. Pat. No. 4,453,909 issued on Jun. 12, 1984 and U.S. Pat. No. 4,438,010 the specifications for which are incorporated by reference herein. Described in said U.S. Pat. No. 4,453,909 and U.S. Pat. No. 4,438,010 is a process for making a tablet of soap containing a perfume containing core, hollow or solid fabricated from a hard plastic material either thermosetting or thermoplastic. The soap from the resulting composite tablet is useable until the core is washed clean and contains functional ingredients, e.g., the repellents described, supra, and optionally, aromatizing agent until the core is washed clean. This obviates the wastage of soap which normally occurs as a conventional soap tablet becomes very thin on use and at the same time gives rise to a continuously functional ingredient-containing soap, (e.g., repellent and optionally aromatizing agent) tablet. Thus, this invention also relates to detergent bars having a plastic core containing one or more of the above described carbocyclic ketones, aldehydes and esters of our invention and optionally a perfume which is not repellent. More particularly, this invention relates to detergent bars intended for conventional toilet soap uses either as hand soaps or bath or shower soaps which are elastic or inelastic in nature but which contain a solid plastic core containing insect repellent and optionally perfume giving them unique properties which alleviate wastage thereof and causes the environment surrounding the soap on use thereof to be both insect repellent and optionally aromatized in an aesthetically pleasing manner.

Yet another aspect of our invention relates to the use of the aforementioned repellents, the carbocyclic ketones, aldehydes and esters of our invention taken further in combination with N-(meta toluyl)-methyl piperidines defined according to the structure:

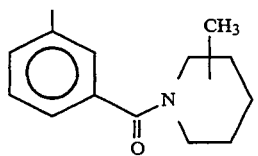

as described in U.S. Pat. No. 3,463,855 issued on Aug. 26, 1969, the specification for which is incorporated by reference herein. The compounds defined according to the structure:

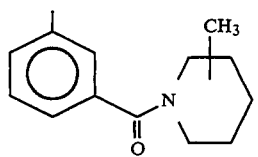

include:
N-(meta-toluyl)-2-methylpiperidine,
N-(meta-toluyl)-3-methylpiperidine, and
N-(meta-toluyl)-4-methylpiperidine.

The proportions of compounds defined according to the structure:

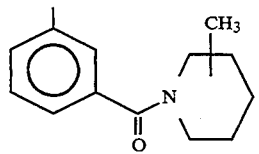

to one or a combination of any of the carbocyclic ketones, aldehydes and esters of our invention are between about 1 part N-(meta-toluyl)methylpiperidine:99 parts carbocyclic ketones, aldehydes and esters of our invention down to 99 parts carbocyclic ketones, aldehydes and esters of our invention:1 part N-(meta toluyl)-methyl piperidines.

In addition, the compositions useful in repelling the Aedes aegyptae of our invention can also contain 1-nonen-3-ol described and claimed in U.S. Pat. No. 4,693,890 and 4,759,228 issued on Jul. 26, 1988, the specifications for which are incorporated by reference herein. The ratio of 1-nonen-3-ol:carbocyclic ketones, aldehydes and esters of our invention useful in repellent compositions may vary from about 1 part 1-nonen-3-ol:99 parts carbocyclic ketones, aldehydes and esters of our invention down to 99 parts 1-nonen-3-ol:1 part carbocyclic ketones, aldehydes and esters of our invention.

In addition to the soap fabrication, another aspect of our invention relates to the formation of repelling articles containing one or more of the carbocyclic ketones, aldehydes and esters of our invention, that is, articles useful for the repelling of mosquitoes (Aedes aegyptae) in combination with compatible polymers (e.g., high density polyethylene or low density polyethylene). Thus, another aspect of our invention provides a process for forming at least one of the carbocyclic ketones, aldehydes and esters of our invention-containing polymeric particles such as foamed polymeric pellets which include a relatively high concentration of at least one of the carbocyclic ketones, aldehydes and esters of our invention as defined, supra.

Thus, another aspect of our invention relates to the formation of a carbocyclic ketone, aldehyde or ester containing polymeric pellets by means of introduction into a single screw or twin screw extruder of, in series, a polymer followed by at least one of the carbocyclic ketones, aldehydes and esters of our invention which is compatible with the thermoplastic polymer and then optionally followed by the introduction of gaseous blowing agent or blowing agent which will produce a gas which is inert to the polymer and to the carbocyclic ketone, aldehyde, or ester previously introduced into the extruder.

The advantage of using a foamed polymeric particle are multiple, to wit:
(i) improved handling;
(ii) greater retention of the carbocyclic ketone, aldehyde or ester when not in use;
(iii) greater length of time during which the release of the carbocyclic ketone aldehyde or ester of our invention from the polymer is at "steady state" or "0 order".

The nature of the extruder utilized in the process of our invention to form the polymeric carbocyclic aldehydes, ketones or esters-containing polymer particles of our invention may be either single screw or double screw. Thus, the types of extruder that can be used are disclosed at pages 246–267 and 332–349 of the Modern Plastics Encyclopedia, 1982–1983, published by the McGraw-Hill Publishing Company, the disclosure of which is incorporated by reference herein. More specifically, examples of extruders which are useable in carrying out one of the processes of our invention (with modification for introduction of at least one of the carbocyclic ketones, aldehydes or esters of our invention) downstream from the introduction of the polymer and with further modification that the gaseous blowing agent is introduced still further downstream from the point of introduction of the carbocyclic ketone, aldehyde or ester of our invention are as follows:

1. The Welex "Super Twinch" 3.5" extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kans. 67277;
3. Modified Sterling model 4000 and 5000 series extruder manufactured by Sterling Extruder Corporation of 901 Durham Avenue, South Plainfield, N.J.;

4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder manufactured by the Werner & Pfleiderer Corporation of 663 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff single screw, twin screw, or foam extrusion equipment manufactured by Berstorff Corporation, P.O. Box 240357, 8200-A Arrowridge Boulevard, Charlotte, N.C. 28224.

In producing the carbocyclic ketone, aldehyde or ester-containing polymer particles of our invention various polymers may be utilized, for example, low density polyethylene, high density polyethylene, polypropylene, the co-polymer of ethylene and vinyl acetate and polyvinylchloride. More specifically, the polymers used in the practice of our invention may be co-polymers of ethylene and a polar vinyl monomer selected from (a) vinyl acetate; (b) ethyl acrylate; (c) methyl acrylate, (d) butyl acrylate and (e) acrylic acid including the hydrolyzed copolymer of ethylene and vinyl acetate. Preferred co-polymers are ethylene-vinyl acetate with about 9 to 60% vinyl acetate and ethylene-ethyl acrylate with about 6 to 18% ethyl acrylate.

Resins of the type disclosed for use as co-polymers are commercially available in the molding powder form. For example, ethylene vinyl acetate co-polymers are marketed by the E. I. dupont Nemours Company under the tradename "ELVAX®" and by the Arco Polymer Division under the trademark "DYLAND®" and by the Exxon Corporation of Linden, N.J. under the trademark "DEXXON®". Ethylene/ethyl-acrylate co-polymers are marked by Union Carbide Corporation under the trademark "EEA RESIN®".

The polymer is added to the single screw or twin screw extruder at a feed rate in the range of from about 80 up to about 300 pounds per hour while maintaining the temperature of the screw extruder between about 160° C. and about 240° C. If the polymer or co-polymer powder is added to the extruder at a reference "barrel segment" then the carbocyclic aidehyde, ketone or ester of our invention is added to the extruder under pressure downstream from the retention point of the polymer at one or more of "barrel segments" (S-2, S-3, S-5, S-6, S-7, S-8 or S-9)(referring to FIG. 2 briefly described, supra, and described in detail, infra).

The proportion of carbocyclic ketone, aldehyde and/or ester (taken further together with other insect repelling materials if desired) to resin can vary from small but effective amounts on the order of about 1% of the weight of resin body up to about 45% by weight of the resin body. In general, it is preferred to use between about 5% up to about 30% based on the weight of the resin body of insect repellent composition of our invention. This is an optimum amount balancing the proportion of insect repellent composition of our invention against the time period over which the article emits the insect repellent composition and against the tendency of the components of the insect repellent composition to oil out either individually or in combination. This "oiling out" is specifically avoided as a result of the use of the foaming agent discussed, infra. Various polymers are useful in the practice of our invention. Specific examples of polymers useful in the practice of our invention are as follows:

(a) DYLAN® brand of low density polyethylene. DYLAN® is a trademark owned by the Atlantic Richfield Company of Los Angles, Calif.;

(b) DYLITE® of expandable polystyrene compositions. DYLITE® a trademark of Atlantic Richfield Company of Los Angeles, Calif.;

(c) SUPER DYLAN® a high density polyethylene. SUPER DYLAN® is a trademark of the Atlantic Richfield Company of Los Angeles, Calif.;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated by reference herein;

(f) Polyene/alpha-olefin as exemplified and disclosed in U.S. Pat. No. 4,369,291, the specification for which is incorporated by reference herein;

(g) Poly-alpha-olefins as exemplified in Canadian Letters Pat. No. 1,137,069 issued on Dec. 7, 1982, the specification for which is incorporated by reference herein;

(h) Polymeric compositions as disclosed in Canadian Letters Pat. 1,137,068 issued on Dec. 7, 1982, the specification for which is incorporated by reference herein;

(i) Poly-alpha-olefins disclosed in Canadian Letters Pat. No. 1,137,067, the specification for which is incorporated by reference herein;

(j) Polyolefins described in Canadian Letters Pat. No. 1,137,066, the specification for which is incorporated by reference herein;

(k) Polyethylene oxides as disclosed in Canadian Letters Pat. No. 1,137,065 issued on Dec. 7, 1982, the specification for which is incorporated by reference herein;

(l) Olefin polymers and co-polymers as disclosed in Canadian Letters Pat. No. 1,139,737, the disclosure for which is incorporated by reference herein. Canadian Pat. No. 1,139,737 was issued on Jan. 18. 1983;

(m) Polyolefins disclosed in Canadian Letters Pat. No. 1,139,738, the disclosure for which is incorporated by reference herein. Canadian Pat. No. 1,139,738 was issued on Jan. 18, 1983;

(n) Chlorinated PVC as disclosed in Polymer 1982, 23 (7, Suppl.), 1051-6 abstracted at Chem.Abstracts 97:14550y, 1982;

(o) Polyepsilon caprolactone co-polymers made by means of alcohol initiated polymerization as disclosed in J.Polym. Sci.Polym.Chem.Ed. 1982, 20(2), pages 319-26, abstracted at Chem.Abstracts, Volume 96:123625x, 1982;

(p) Styrene acrylonitrile co-polymers as disclosed in Diss. Abstracts, Int. B, 1982, 42(8), 3346 and abstracted at Chem. Abstracts 96:143770n (1982);

(q) Co-polymers of epsilon caprolactone with 1,4-butane diol as disclosed at Kauch Rezine, 1982, (2), 8-9, abstracted at Chem.Abstracts, Volume 96:182506g (1982);

(r) Polyesters as disclosed in U.S. Pat. No. 4,326,010, the specification for which is incorporated by reference herein;

(s) Chlorinated polyethylene as disclosed by Belorgey, et al, J.Polym.Sci.Plym.Phys.Ed. 1982, 20(2), 191-203;

(t) Plasticized polyepsilon caprolactone co-polymers containing dimethyl phthalate plasticizers as set forth in Japanese Pat. No. J81/147844, abstracted at Chem. Abstracts, Volume 96:69984y, (1982), the specification for which is incorporated by reference herein;

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyuretane polymers having lactone backbones as disclosed in U. S. Pat. No. 4,156,067 issued on May 22, 1979, the disclosure of which is incorporated by reference herein;

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

Downstream from the addition point of the carbocyclic aidehyde, ketone or ester of our invention taken alone or taken further together with other insect repellents, optionally, the gaseous or liquid containing blowing agent may be added (e.g., at "barrel segments" (S-5, S-6, S-7, S-8, S-9 or S-10)) using the polymer addition "barrel segment" as a reference "barrel segment" S-1.

Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gase, e.g., hydrogen, should be avoided. The pressure of the gase blowing agent being added to the extruder at the point of addition may vary from about 80 up to about 150 psig. Higher pressures may be used without adversely affecting the usefulness of the foamed insect repellent composition-containing article.

The feed rate range of insect repellent composition-containing but not limited to at least one of the carbocyclic aldehydes, ketones or esters of our invention, may be between about 0.5% up to about 45% by weight of the polymer.

The die of the extruder may create rod, sheet, film or ribbon. The resulting product may then, if desired, be pelletized to form insect repellent composition-containing polymer particles or the ribbon may be used "as is" as an insect repellent-containing polymeric article of manufacture itself.

In addition to the optional gaseous blowing agents (which are necessarily "inert" gases), blowing agents may be added at the same point on the extruder which will create gaseous voids in the insect repellent-containing polymer articles of our invention and these "blowing agents" are well known to one having ordinary skill in the art. Examples of such non-gaseous containing materials which yield gases on admixture with the polymer in the extruder but which are still inert to the insect repellent are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CFCl_3$, $CF_2Cl_2$, $CH_3Cl_1l$, $CH_2Cl_2$ separately or in admixture with one another as set forth in U.S. Pat. No. 3,758,425, column 4, lines 1–5, the specification for which is incorporated by reference herein;

(iii) Dichlorotetrafluoroethane, tetramethylmethane, monochlorodifluoromethane, dichlorodifluoromethane, and dichlorotetrafluoroethane as specifications described in U.S. Pat. Nos. 2,948,664 and 2,948,665 issued on Aug. 9, 1990, the specifications for which are incorporated herein by reference; and (iv) Azo bis(formamide); diazoaminobenzene, N,N'-dinitrosopentamethylene tetramine; N,N'-dimethyl-N,N'-dinitrosoterephthalamide; p,p'-oxy-bis (-benzene sulfonyl semicarbazide; azo bis-(isobutyronitrile); p,p'-oxy-bis(benzene sulfonyl hydrazide ); p,p'-diphenyl-bis(sulfonyl hydrazide); benzene-sulfonyl hydrazide; m-benzene-bis-(sulfonyl hydrazide) as more specifically described in U.S. Pat. No. 3,298,975 issued on Jan. 17, 1967, the specification for which is incorporated by reference herein.

The resulting extruded (and, if desired, pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

In addition, our invention relates to candle body materials which on use are both insect repellent and perfuming which contain one or more of the carbocyclic aldehydes, ketones or esters of our invention and optionally other insect repellent materials including, for example, at least one of the compounds having the structure:

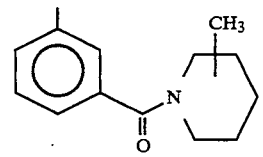

in order to repel the mosquito species, *Aedes aegyptae*.

The mosquito repellent perfuming compositions which form part of the candle body materials are within the following specifications:

(I) from 5 up to 100% by weight of an efficacious perfuming/insect repellent composition containing at least one of the carbocyclic aldehydes, ketones or esters of our invention; and (II) from 0 up to 95% by weight of a standard perfuming substance (non-insect repellent or insect repellent) which may be one or a combination of the following materials:

the methyl ester of 2,5-dihydroxy-4,6-dimethyl benzoic acid;
dihydro myrcenol;
oakmoss absolute;
geraniol;
isobornyl acetate;
citronellyl acetate;
para-t-butyl phenyl isovaleraldehyde;
benzyl salicylate;
hexyl cinnamic aidehyde;
geranonitrile;
patchouli oil;
alpha-terpineol;
tetrahydromuguol;
phenyl ethyl alcohol;
cedrenal;
methyl ionone;
cinnamyl acetate;
benzyl benzoate;
L-Citronellal;
nerol;
geranyl formate;
geranyl acetate;
eugenol;
alpha Farnesene;
beta Farnesene;
citral;
n-Nonanal; and
n-Octanal.

The foregoing formula may require a solubilizing agent, e.g., the methyl ester of dihydroabietic acid (commercial name: HERCOLYN D ®) benzyl benzoate isopropyl myristate and/or $C_{12}$-$C_{14}$ isoparaffin hydrocarbons.

The candle base composition can be standard paraffin wax, or it can be transparent or pastel shaded as more particularly described in U.S. Pat. No. 3,615,289 issued on Oct. 26, 1971 (the disclosure of which is incorporated by reference herein) and wherein the candle body comprises as the basic components a mixture of:

(i) a thermoplastic polyamide resin formed from linoleic acid polymerized with a polyamine compound;
(ii) an alkanol amide or alkanol amine; and
(iii) a stearic acid compound.

The weight ratio of candle body: insect repellent/perfumant substance of our invention may vary from about 0.8% up to about 10% with a range of from about 0.8% up to about 2.0% being preferred when no non-insect repelling perfume oil is used in conjunction with at least one of the carbocyclic ketones, aldehydes and/or esters of our invention; and with a range of from about 1.5% up to about 10% by weight of the overall composition being preferred when a non-insect repelling perfume oil is used in conjunction with at least one of the carbocyclic ketones, aldehydes and/or esters of our invention.

Specifically, the polyamide may be a "VERSAMID" resin which is a thermoplastic condensation product of polymerized linoleic acid with various polyamine compounds such as ethylene diamine, ethylene triamine and the like. Specific "VERSAMID" compounds are "VERSAMID ®900", "VERSAMID ®930", "VERSAMID ®940", "VERSAMID ®948", "VERSAMID ®950" and "VERSAMID ®1635".

These compounds are products of the Henkel Chemical Corporation of Minneapolis, Minn.

Another substance required in the clear candle composition consists of about 20–55% by weight of an alkanol amine or alkanol amide prepared by the reaction of a fatty acid ester and amine whereby the ester and the amine are in substantially equal proportions, for example, compounds such as BARLOL ® 12C2 (manufactured by the Barrid Chemical Company) a monoalkyl diethanolamine have 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. These stearic acid compounds serve as stabilizing agents which permit the ready incorporation of the insect repellent/perfumant compositions of our invention up to a level of approximately 5% (total proportion of perfume oil-insect repellent composition). They are carriers for the perfumant/insect repellent and may be used in a proportion of between 1 and 50% by weight of the composition although the preferable range is between 20 to 30%. In this connection it is possible to use up to about 10% by weight of a perfumant/insect repellent if part of the formula is replaced by the material "NEVEX ®100", a product which is a coumarin-indene copolymer resin of very little unsaturation manufactured by the Neville Chemical Company.

Rather than being a crystalline paraffin wax the candle base of our invention may be an oil gel that has as its base a light mineral oil, an inexpensive natural oil or a combination of such oils which oil gel has a non-greasy surface and feel and sufficient rigidity to be self-supporting at room temperatures. Such a gel is disclosed in U.S. Pat. No. 3,645,705 issued on Feb. 29, 1972, the disclosure of which is incorporated by reference herein. Such compositions of matter include:

(a) from about 35% up to abut 85% by weight of an oil which is normally liquid at room temperature chosen from the group consisting of light mineral oils and natural oils having iodine values substantially within the range of 40–135;
(b) from about 7% up to about 40% by weight of a long chain polyamide having a molecular weight substantially within the range of 6000–9000 and a softening point substantially within the range of 18° C.–48° C.; and
(c) from about 7% up to about 30% of an alcohol selected from the group consisting of 8 to 12 carbon primary alcohols.

DETAILED DESCRIPTION OF THE DRAWINGS

Tests for determining insect (*Aedes aegyptae*) attractancy or repellency are carried out using an olfactometer as shown in detail in FIG. 1. Referring to FIG. 1, FIG. 1 sets forth an olfactometer embodiment wherein the olfactometer is assisted with computer apparatus shown in schematic form and block flow diagram form using reference numerals 3520, 3521, 3523 and 3524. Thus, FIG. 1 sets forth in perspective an exploded view of olfactometer apparatus useful in connection with determining data for our invention, that is, used in testing the efficacy of, for example, the LAVONAX ™, the CYCLEMONE A ™, the methyl anthranilate or the MELOZONE ™ taken alone or in conjunction with one another, as mosquito (*Aedes aegyptae*) repelling materials.

Air supply source 3634 provides air to mixing station 3636 wherein the air is mixed with treatment agent from treatment agent source 3635 (source of, for example, LAVONAX TM ). The resulting mixture passes through tube 3636g (for example) and enters the apparatus through side portals. The entry is through spacer plate 3628 and above base plate 3625. The entry of the air-treament agent is in a direction parallel to the surface of the base plate 3625. Thus, the base plate 3625 is separated from the spacer plate 3629 for the air-treament agent (e.g., CYCLEMONE A TM ). The air exit is indicated by reference numeral 3537. Simultaneously with the supplying of air and treatment agent from mixing station 3636, light is supplied from beneath the enclosed insect feeding and/or stimulating means collectively denoted as "IFS" means through light guides 3652, from light source 3551 which is powered by electric power supply 3550 marketed by RADIO SHACK ®, Division of Tandy Corporation of Forth Worth, Tex. 76102 under the trademark ARCHER ®, Catalog No. 276-228 ("1.0 mm optical plastic fiber length 5 meters"). An example of light source 3551 is KRATOS Monochromatic Illuminator GM 100 Miniature VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. Another light supply source is the KRATOS GM 200 Double Grating Monochromator. Another example of a useful light source is the KRATOS GM 252 High Intensity Grating Monochromator. The base plate 3625 is also separated from the spacer plate 3629 for the light guides 3652 whereby the light guides 3652 are held in place in the base plate 3625 whereby the light (or other forms of radiation) is directed in a direction perpendicular to the electrical sensor element 3610. Air supply source from location 3634 and treatment agent from location 3635 is mixed at a mixing station 3636 where upon treatment agent and air in admixture is passed through lines 3636a and 3636g through portals located in the spacer element 3628 in a direction along the directional vector parallel to the electrical sensing element 3610.

When an insect lands on a grid of a sensoring element a landing is recorded electrically through a sensor. The sensor causes an electrical impulse caused by the pressure of the insect's (*Aedes aegyptae*, for example) landing to proceed through wires 3619a and 3619b to an electrically biased differential amplifier 3639 (using electric power supply 3539 also connected to wire 3619c which is connected to the electrode 3679 which is immersed in the feeding stimulant composition or stimulant for the insect 3674, and then to a multi-channel A.C. converter 3523. Converter 3523 is associated with program tape storage 3524, printer 3520 and data link to digital computer 3521. Such apparatus is described in detail in U.S. Pat. No. 5,165,926 issued on Nov. 24, 1992, the specification for which is incorporated by reference herein.

Figure 2:
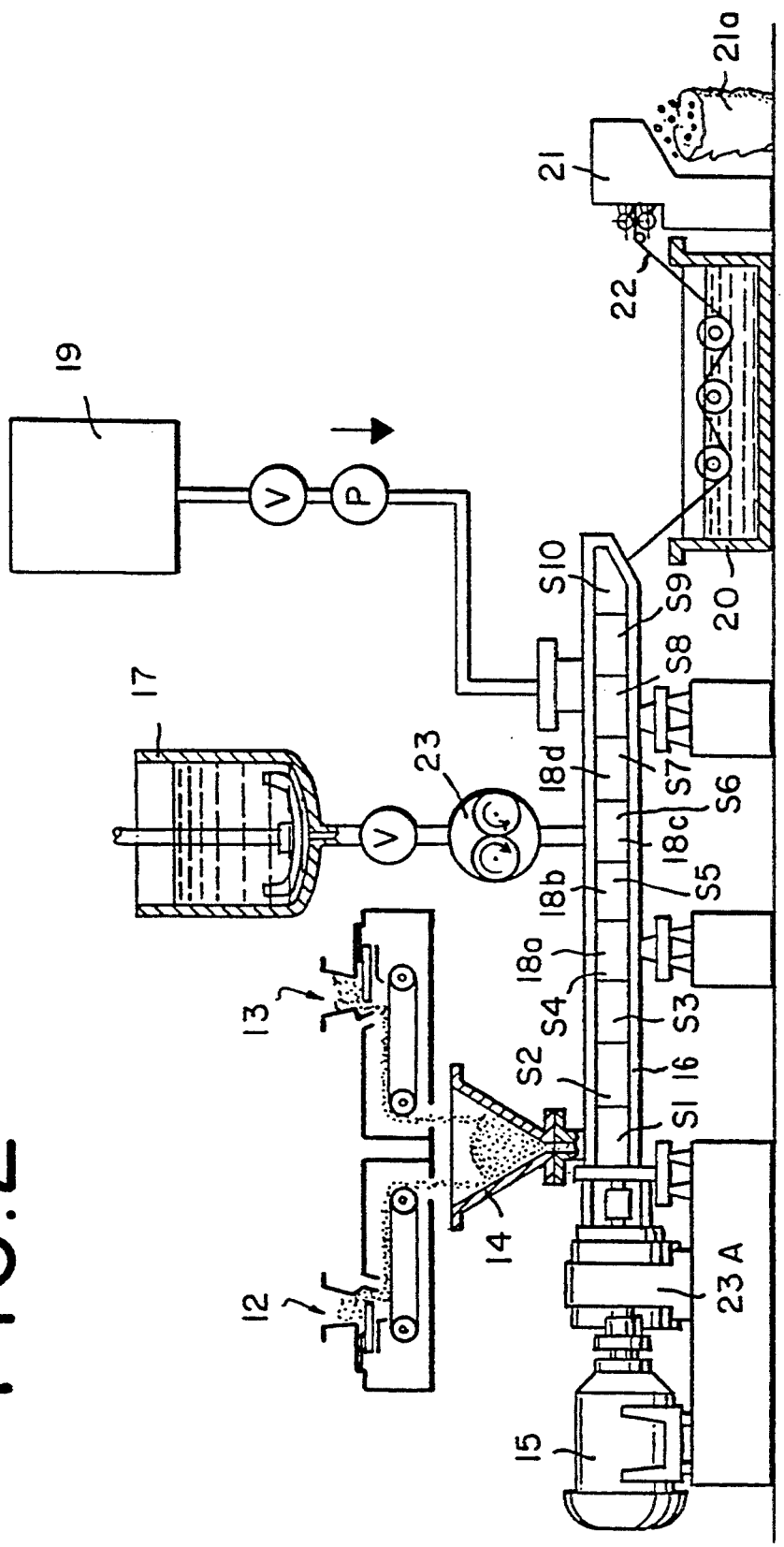
FIG. 2 is a cut-away side elevation schematic diagram of a screw extruder during the compounding of a resin with insect repellents including one or more of the carbocyclic ketones, aldehydes or esters of our invention while simultaneously adding foaming agent into the hollow portion of the barrel of the extruder and incorporates the pelletizing apparatus used in the pelletizing of the extruded foamed tow product produced as a result of the extrusion operation.

FIG. 2 is a schematic cut-away elevation diagram of an extrusion and pelletizing apparatus useful in carrying out a process of our invention during the operation of said apparatus whereby the insect repellent is incorporated into a polymer such as polyethylene. Motor 15 drives the extruder screws located at 23A in barrel 16, the extruder being operated at temperatures in the range of from about 150° C. up to about 250° C. At the beginning of the barrel, resin at source 12 together with additives, e.g., processing aids and densifiers at location 13 is added via addition funnel 14 into the extruder. Simultaneously (when the operation reaches "steady state"), insect repellent, e.g, LAVONAX ®, CYCLEMONE A ®, methyl anthranilate and/or MELOZONE TM is added to the extruder at one or more barrel segments S-3, S-4, S-5, S-6, S-7 and S-8 of the extruder (which may be a twin screw or a single screw extruder) at locations 18a, 18b, 18c and 18d (for example) by means of gear pump 23 from source 17. From source 19 into barrel segments S-5, S-6, S-7, S-8, S-9 and S-10, a gaseous or liquid blowing agent, e.g., nitrogen, carbon dioxide and the like as described, supra, are added simultaneously with the addition of the insect repellent, e.g., one or more of the carbocyclic ketones, aldehydes or esters of our invention. The feed rate range of the resin is about 80–300 pounds per hour. The feed rate range of insect repellent is between 1 and 35% of the feed rate range of the resin. The blowing agent range is such that the pressure of the gas or the pressure over the liquid being fed into the extruder is between about 50 and 200 psig, if, indeed, blowing agent is added. If desired the extruded ribbon or cylinder may be passed through water bath 20 and pelletizer 21 into collection apparatus 21a.

FIG. 3A is a series of graphs depicted in three dimensions (in a rectangular mode for the "x" and "y" axes) showing the relative attractiveness or repellency of several compositions of matter. The graph indicated by reference numeral 30a is for methyl anthranilate having the structure:

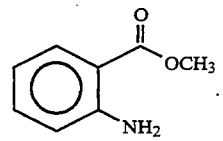

The graph indicated by reference numeral 32a is for air. The graphs show the attractancy or repellency for the mosquito species *Aedes aegyptae* using the apparatus of FIG. 1. The graphs are based on experiments run for a total of one hour with six intervals of ten minutes each. The results are tabulated in Table I(A) as follows:

TABLE I(A)

| Composition Tested | Graph No. | Insects Collected Per Interval | | | | | |
|---|---|---|---|---|---|---|---|
| Methyl anthranilate | 30a | 0 | 0 | 0 | 0 | 0 | 0 |
| Air | 32a | 68 | 87 | 204 | 105 | 97 | 227 |

FIG. 3B is a series of graphs depicted in three dimensions (in a rectangular mode for the "x" and "y" axes) showing the relative attractiveness or repellency of several compositions of matter. The graph indicated by reference numeral 30b is for methyl anthranilate. The graph indicated by reference numeral 32b is for air. The graphs show the attractancy or repellency for the mosquito species Aedes aegyptae using the apparatus of FIG. 1. The graphs are based on experiments run for a total of six hours with six intervals of one hour each. The results are tabulated in Table I(B) below as follows:

TABLE I(B)

| Composition Tested | Graph No. | Insects Collected Per Interval | | | | | |
|---|---|---|---|---|---|---|---|
| Methyl | 30b | 0 | 0 | 0 | 0 | 0 | 0 |

TABLE I(B)-continued

| Composition Tested | Graph No. | Insects Collected Per Interval | | | | | |
|---|---|---|---|---|---|---|---|
| anthranilate | | | | | | | |
| Air | 32b | 227 | 142 | 205 | 229 | 175 | 256 |

FIG. 3C is a series of graphs depicted in three dimensions (in a rectangular mode for the "x" and "y" axes) showing the relative attractiveness or repellency of several compositions of matter. The graph indicated by reference numeral 30c is for methyl anthranilate. The graph indicated by reference numeral 32c is for air. The graphs show the attractancy or repellency for the mosquito species *Aedes aegyptae* using the apparatus of FIG. 1. The graphs are based on experiments run for a total of twelve hours with six intervals of two hours each. The results are tabulated in Table I (C) as follows:

TABLE I(C)

| Composition Tested | Graph No. | Insects Collected Per Interval | | | | | |
|---|---|---|---|---|---|---|---|
| Methyl anthranilate | 30c | 1 | 4 | 0 | 0 | 0 | 1 |
| Air | 32c | 226 | 383 | 374 | 340 | 289 | 292 |

FIG. 4A is a series of graphs depicted in three dimensions (in a rectangular mode for the "x" and "y" axes) showing the relative attractiveness or repellency of several compositions of matter. The graph indicated by reference numeral 40a is for LANONAX TM having the structure:

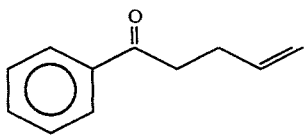

The graph indicated by reference numeral 41a is for MELOZONE TM, defined according to the structure:

a 50:50 mixture of the compound having the structure:

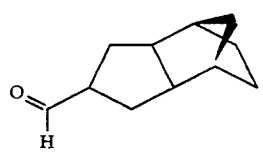

and the compound having the structure:

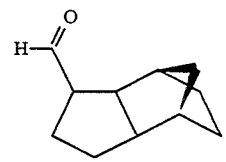

The graph indicated by reference numeral 42a is for air. The graph indicated by reference numeral 43a is for a mixture containing 81 mole percent geraniol having the structure:

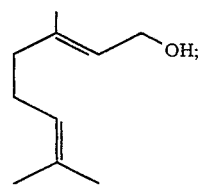

14 mole percent citronellol having the structure:

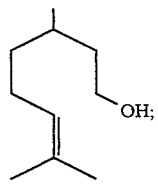

and 5 mole percent nerol having the structure:

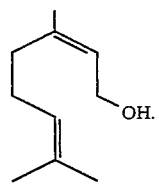

The graphs shows the attractancy or repellency for the mosquito species *Aedes aegyptae* using the apparatus of FIG. 1. The graphs are based on experiments run for a total of one hour with six intervals of ten minutes each. The results are tabulated in Table II(A) as follows:

TABLE II(A)

| Composition Tested | Graph No. | Insects Collected Per Interval | | | | | |
|---|---|---|---|---|---|---|---|
| LAVONAX TM | 40a | 8 | 3 | 1 | 0 | 0 | 0 |
| MELOZONE TM | 41a | 9 | 0 | 0 | 5 | 15 | 0 |
| Air | 42a | 74 | 148 | 168 | 88 | 144 | 125 |
| 81 mole %: 14 mole %: 5 mole % mixture of geraniol: citronellol: nerol | 43a | 3 | 1 | 1 | 0 | 0 | 0 |

FIG. 4B is a series of graphs depicted in three dimensions (in a rectangular mode for the "x" and "y" axes) showing the relative attractiveness or repellency of several compositions of matter. The graph indicated by reference numeral 40b is for LAVONAX TM. The graph indicated by reference numeral 41b is for MELOZONE ™. The graph indicated by reference numeral 42b is for air. The graph indicated by reference numeral 43b is for the 81 mole percent:14 mole percent:5 mole percent mixture of geraniol:citronellol:-nerol. The graphs shows the attractancy or repellency for mosquitoes *Aedes aegyptae* using the apparatus of FIG. 1. The graphs are based on experiments run for a total of six hours with six intervals of one hour each. The results are tabulated in Table II(B) below:

TABLE II(B)

| Composition Tested | Graph No. | Insects Collected Per Interval | | | | | |
|---|---|---|---|---|---|---|---|
| LAVONAX ™ | 40b | 0 | 2 | 0 | 22 | 29 | 71 |
| MELOZONE ™ | 41b | 0 | 2 | 15 | 8 | 0 | 0 |
| Air | 42b | 125 | 158 | 93 | 224 | 133 | 246 |
| 81 mole %: 14 mole %: 5 mole % mixture of geraniol: citronellol: nerol | 43b | 0 | 0 | 0 | 0 | 0 | 0 |

FIG. 5A is a series of graphs depicted in three dimensions (in a rectangular mode for the "x" and "y" axes) showing the relative attractiveness or repellency of several compositions of matter. The graph indicated by reference numeral 50a is for CYCLEMONE A ™, a mixture of 51 mole percent of the compound having the structure:

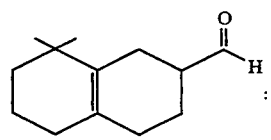

17 mole percent of the compound having the structure:

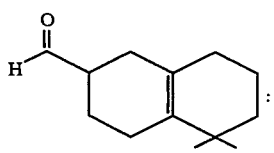

and 32 mole percent of the compound having the structure:

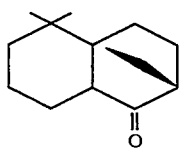

The graph indicated by reference numeral 52a is for air. The graph indicated by reference numeral 53a is for a mixture containing 81.8 mole percent geraniol having the structure:

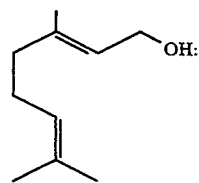

11.66 mole percent citronellol having the structure:

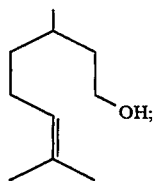

and 6.53 mole percent nerol having the structure:

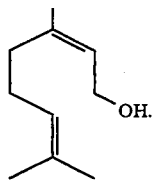

The graphs show the attractancy or repellency for the mosquito species *Aedes aegyptae* using the apparatus of FIG. 1. The graphs are based on experiments run for a total of one hour with six intervals of ten minutes each. The results are tabulated in Table III(A) as follows:

TABLE III(A)

| Composition Tested | Graph No. | Insects Collected Per Interval | | | | | |
|---|---|---|---|---|---|---|---|
| CYCLEMONE A ™ | 50a | 1 | 2 | 0 | 1 | 0 | 4 |
| Air | 52a | 43 | 47 | 232 | 107 | 144 | 68 |
| 81.8 mole %: 11.66 mole %: 6.53 mole % mixture of geraniol: citronellol: nerol | 53a | 4 | 0 | 20 | 0 | 0 | 0 |

FIG. 5B is a series of graphs depicted in three dimensions (in a rectangular mode for the "x" and "y" axes) showing the relative attractiveness or repellency of several compositions of matter. The graph indicated by reference numeral 50b is for CYCLEMONE A ™. The graph indicated by reference numeral 52b is for air. The graph indicated by reference numeral 53b is for an 81.8 mole percent:11.66 mole percent:6.53 mole percent mixture of geraniol:citronellol:nerol. The graphs show the attractancy or repellency for the mosquito species *Aedes aegyptae* using the apparatus of FIG. 1.

The graphs are based on experiments run for a total of six hours with six intervals of one hour each. The results are tabulated in Table III(B) as follows:

TABLE III(B)

| Composition Tested | Graph No. | Insects Collected Per Interval | | | | | |
|---|---|---|---|---|---|---|---|
| CYCLEMONE A ™ | 50b | 4 | 1 | 0 | 1 | 4 | 1 |
| Air | 52b | 68 | 44 | 85 | 70 | 52 | 165 |

TABLE III(B)-continued

| Composition Tested | Graph No. | Insects Collected Per Interval | | | | | |
|---|---|---|---|---|---|---|---|
| 81.8 mole %: 11.66 mole %: 6.53 mole % mixture of geraniol: citronellol: nerol | 53b | 0 | 0 | 1 | 1 | 20 | 8 |

EXAMPLE I

PARAFFIN WAX CANDLE BODY

The following composition is prepared:

| Ingredients | Parts by Weight |
|---|---|
| Paraffin Wax | 95.0 |
| 50:50 Mixture of LAVONAX TM having the structure: | 5.0 |

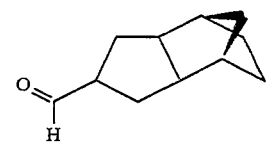

and

Methyl anthranilate having the structure:

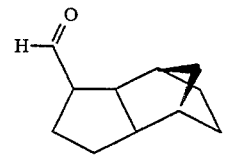

Paraffin wax is intimately admixed at 150° C. and 10 atmospheres pressure with the mixture of LAVONAX TM and Methyl anthranilate in an autoclave with intensive shaking. The autoclave pressure is maintained with a nitrogen atmosphere. At the end of the period of 1 hour the autoclave is depressurized, the autoclave is opened and the resulting mixture is poured into cylindrical candle molds containing wicks.

The resulting candles on use evolve an aesthetically pleasing aroma and, in addition, give rise to efficacious mosquito repellency (*Aedes aegyptae*). The candles are effective in preventing mosquitoes from entering a room in which one candle is burning for a period of 10 minutes, the said room having the dimensions 6'×15'×15'having a 3'×3'open portal adjacent to a mosquito (*Aedes aegyptae*)-infested region in the month of August in the temperate zone (location: Highlands, N.J. next to Raritan Bay).

EXAMPLE II

A transparent candle base mixture is produced by intimately admixing the following ingredients:

| Ingredients | Parts by Weight |
|---|---|
| VERSAMID ® 1635 | 34.0 |
| Barlol 12C2 | 51.0 |
| Butyl Stearate | 3.5 |
| NEVEX ® 100 | 5.0 |
| SPAN ® | 1.5 |
| Isopropyl Isostearate | 4.0 |

-continued

| Ingredients | Parts by Weight |
|---|---|
| Isopropyl Myristate | 4.0 |

The foregoing mixture is placed in an autoclave and intimately admixed with a perfuming-insect repelling composition containing 3 parts by weight of a mixture containing 60% of the compound having the structure:

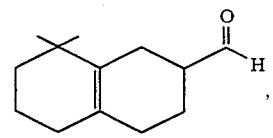

and 40% of the compound having the structure:

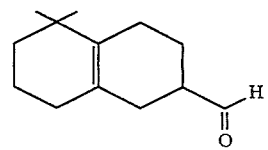

(MELOZONE TM) and 4 parts by weight of CYCLEMONE A TM a mixture containing 51 mole percent of the compound having the structure:

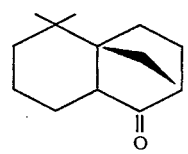

17 mole percent of the compound having the structure:

and 32 mole percent of the compound having the structure:

at the rate of 8% by weight of the total candle base composition.

The autoclave is sealed and heated to 180° C. under 15 atmospheres pressure and maintained with vigorous shaking for a period of 5 hours. At the end of the 5 hour period, the autoclave is depressurized (being under a nitrogen pressure atmosphere) and the autoclave is opened and the contents are then poured into cylindrical candle molds four inches in height and two inches in diameter containing 0,125" wicks. The resulting candles have efficacious mosquito (*Aedes aegyptae*) repellencies and have aesthetically pleasing aromas on use.

The candles are effective in preventing mosquitoes (*Aedes aegyptae*) from entering a room in which two candles have been burning for 15 minutes, the said room having dimensions of 6'×15'×15' and having a 3'×3' open portal adjacent a mosquito (*Aedes aegyptae*)-infested region in the month of August, in the temperate zone of Highlands, N.J. adjacent Raritan Bay.

What is claimed is:

1. An insect repellent candle containing a candle base and intimately admixed therewith an insect repelling quantity of at least one composition of matter selected from the group consisting of:

(i) a mixture of compounds defined according to the structure:

containing from 60–40 mole percent of the compound having the structure:

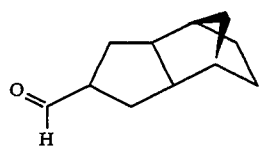

and from 40–60 mole percent of the compound having the structure:

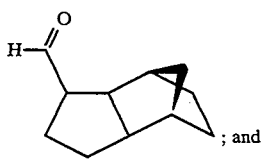
; and (ii) a compound having the structure:

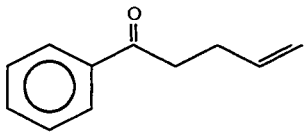

* * * * *